United States Patent [19]

Vermeiren et al.

[11] Patent Number: 4,768,380

[45] Date of Patent: Sep. 6, 1988

[54] METHOD AND MEANS FOR DETECTING FAULTS OR DEFECTS IN MOVING MACHINE PARTS

[75] Inventors: Karel N. Vermeiren, Woerden; Adrianus J. Smulders, Amersfoort, both of Netherlands

[73] Assignee: SKF Engineering & Research Centre, B.V., Nieuwegein, Netherlands

[21] Appl. No.: 935,276

[22] Filed: Nov. 26, 1986

[30] Foreign Application Priority Data

Nov. 28, 1985 [NL] Netherlands ............... 8503294

[51] Int. Cl.$^4$ .............. G01H 1/00; G01M 13/04
[52] U.S. Cl. .................... 73/593; 340/682
[58] Field of Search ........... 73/587, 593, 660, 661; 340/682, 683

[56] References Cited

U.S. PATENT DOCUMENTS 4,088,907  5/1978  Jones et al. ............... 73/587
4,592,034  5/1986  Sachse et al. ............. 73/587

FOREIGN PATENT DOCUMENTS 0600437  4/1978  U.S.S.R. .................. 73/593
0676897  7/1979  U.S.S.R.
1603190  11/1981  United Kingdom.

OTHER PUBLICATIONS

R. C. McMaster, *Nondestructive Testing Handbook* (1982) pp. 630–631.
Maksimov, V. P., Karasev, V. A., Solorer, B. P., "Flaw Detector for Rotating Parts," (21.10.71) Bul. 25/19.8.71.

Primary Examiner—Stewart J. Levy
Assistant Examiner—Lawrence G. Fess
Attorney, Agent, or Firm—Eugene E. Renz, Jr

[57] ABSTRACT

A method for detecting faults or defects in moving machine parts wherein mechanical vibrations produced by a fault or defect are converted into an electrical signal from which the condition of the machine part is obtained. For converting the mechanical vibrations into an electrical signal, an acoustic-emission transducer with wide bandwidth is used. A frequency range in the electrical signal is selected where the half wavelength is smaller than the smallest linear dimension of the cross section of the transducer face which is in contact with the machine part.

6 Claims, 1 Drawing Sheet

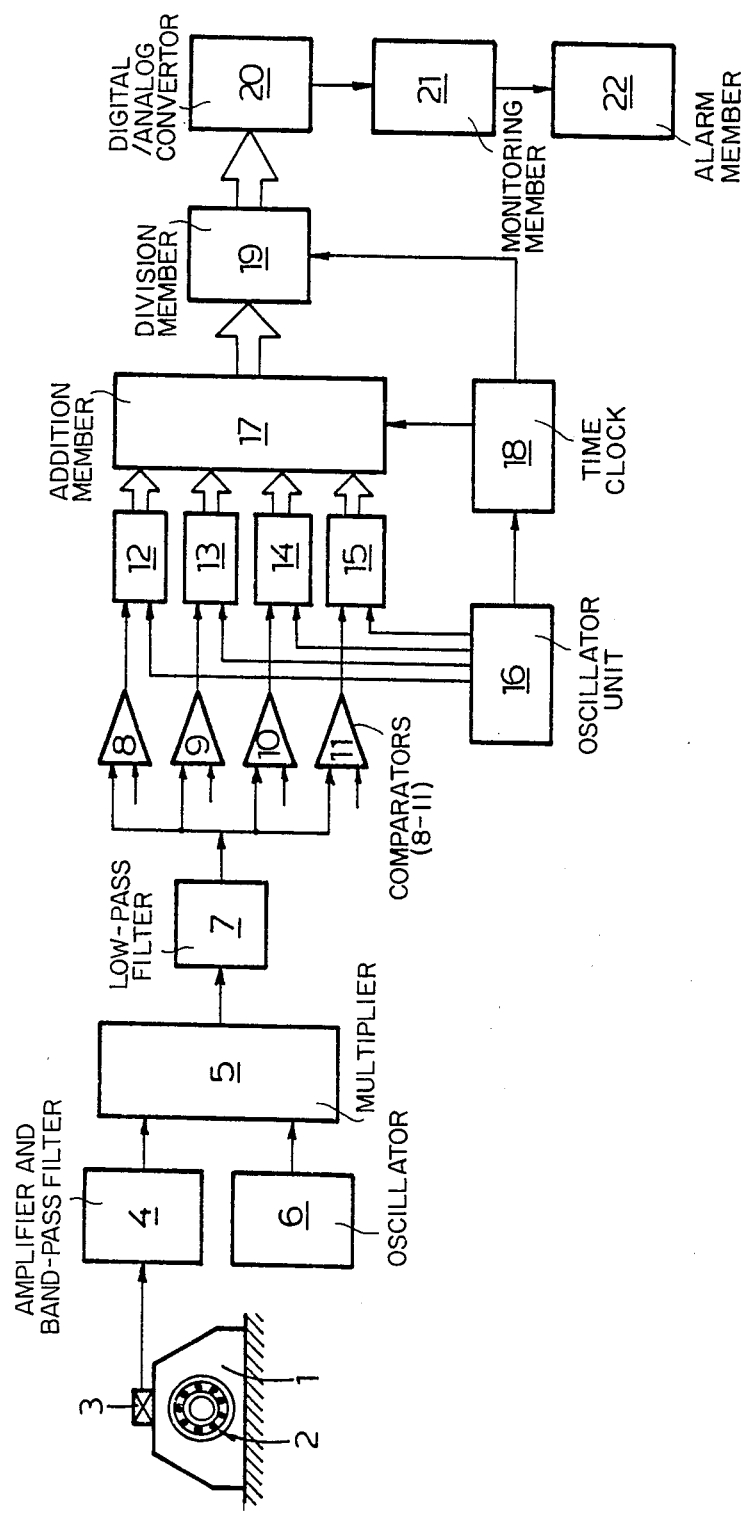

METHOD AND MEANS FOR DETECTING FAULTS OR DEFECTS IN MOVING MACHINE PARTS

FIELD OF THE INVENTION

The invention relates to a method for detecting faults or defects in moving machine parts, wherein mechanical vibrations produced by a fault or defect between the moving parts at the points or surfaces of contact are sensed and converted into an electrical signal from which the condition of the machine part is obtained, as well as a means for the application of this method, provided with a transducer which converts the mechanical vibrations produced by a fault or defect into an electrical signal, and a processing circuit which as a function of this signal emits an output signal that indicates the condition of the machine part.

BACKGROUND OF THE INVENTION

A method and means for detecting faults or defects in moving machine parts are disclosed in British Pat. No. 1,603,190. In this known means, the transducer, which is a mechanically tuned accelerometer, is tuned so that its resonance frequency lies in the range of 30-40 kHz, so that the greatest sensitivity of this transducer likewise lies in this frequency range. This is coincident with the resonant frequency range of the expected vibrations. In this known method and means, use is made of the resonance peak of the transducer to improve the selectivity and amplification. In practice, however, problems arise when bearings of average size, for example, are tested for defects by detecting the mechanical vibrations, because their resonant frequencies and the second and third harmonics thereof all lie in the same frequency range of 30-40 kHz. Thus, the mechanical amplification of given frequency bands in a machine part on which the measurement is being made may be greater than the mechanical amplification of the transducer. The means described in British Pat. No. 1,603,190 is, accordingly, sensitive to disturbance signals making reliable detection of faults and defects impossible. The vibrations that are generated by faults or defects cause standing waves to be produced on the surface of the machine on which the transducer is mounted. The wavelength for frequencies of 40 kHz, for example, is 150 mm, making it difficult to determine a suitable position for the transducer, since there is the chance that the transducer will be placed at a node and nothing would be measured.

The object of this invention is to provide a method and means for detecting faults or defects in moving machine parts wherein these disadvantages are avoided in a simple but nevertheless effective way.

SUMMARY OF THE INVENTION

For this purpose, the present invention is characterized in that for converting the mechanical vibrations into an electrical signal, an acoustic-emission transducer with a wide bandwidth is used and a frequency range in the electrical signal is selected where the half wavelength is smaller than the smallest linear dimension of the cross section of the transducer face which is in contact with the machine part. In the case of a round transducer, that dimension would be the diameter.

The means pursuant to the invention is for this purpose characterized in that the transducer is designed as a wideband acoustic-emission transducer wherein the processing circuit selects a frequency range in the transducer signal where the half wavelength is smaller than the smallest linear dimension of the cross section of the transducer face contacting the machine part.

In this way, a method and means are obtained wherein the transducer may, without any problems, be mounted at any desired location on the machine on which a measurement must be made. In a practical size of the transducer, the frequency range will lie at a frequency at least twice as high as the frequency range of 30-40 kHz, so that disturbances from the resonance frequencies lying in the latter frequency range and the second and third harmonics thereof are no longer experienced.

BRIEF DESCRIPTION OF THE DRAWINGS

These and other objects of the present invention and the various features and details of the operation and construction thereof are hereinafter more fully set forth with reference to the accompanying drawing, wherein an exemplified embodiment is schematically represented.

DETAILED DESCRIPTION OF THE PREFERRED EMBODIMENT

A machine 1, indicated schematically, is provided with a bearing 2 which must be checked for faults or defects. For this purpose, an acoustic transducer 3 with a wide bandwidth is mounted on the machine 1. The acoustic transducer converts the mechanical vibrations of the machine into an electrical signal. Mechanical vibrations are produced, for example, when a defect in the track of the inner or outer race is contacted by the balls of the bearing 2.

The signal from the transducer 3 is fed into an amplifier 4 with a band-pass filter. The output of the amplifier 4 and the output of an oscillator 6 are fed into a multiplier 5. The central frequency of the band-pass filter of the amplifier 4 corresponds to the oscillation frequency of the oscillator 6. A suitable commercially available oscillator has an oscillation frequency of 455 kHz. The output of the multiplier 5 is connected with a low-pass filter 7 having a bandwidth of, for example, 3 kHz. The output signal of the low-pass filter 7 then corresponds to the frequency range of 452-458 kHz in the output signal of the transducer 3. The presence of a defect in the bearing 2 then appears as an amplitude increase in the output signal of the low-pass filter 7.

The means described has several important advantages in that a relatively high oscillator frequency is used so that the resonant second and third harmonic frequencies of the bearing 2 are no longer present. In addition, the half wavelength at this frequency is approximately 12 mm, while the transducer 3 has a diameter which is greater than 12 mm, so that a maximum of a standing wave will always appear in the contact surface of the transducer 3. When transducer 3 has a cross section at the face (in contact with the machine part) which is not round, the smallest linear dimension will be larger than the half wavelength. Here, that length would be greater than 12 mm.

In the example represented of the means pursuant to the invention, the output signal of the low-pass filter 7 is supplied to four comparators 8-11, which compare this output signal with a higher threshold value in each instance. The outputs of the comparators 8-11 are connected to the port input of associated counters 12-15, the clock inputs of which are connected to an oscillator unit 16. The oscillator unit 16 supplies four unlike frequencies 1, 2, 4 and 8 MHz respectively. The counter that receives the clock signal with the lowest frequency is connected by its port input to the comparator with the lowest threshold value, while the counter that receives the clock signal with the highest frequency is connected to the comparator with the highest threshold value. This ensures that the higher amplitudes in the output signal of the low-pass filter 7 are weighed more heavily than the lower amplitudes. The positions of the counters 12–15 that are reached after a fixed time interval are added up by an addition member 17. The time interval is determined by a time clock 18, the time interval being adjustable, for example, to 1, 2, 4 and 6 s. In order to obtain a uniform scale, the total value of the addition member 17 is divided by means of a division member 19 by the time interval selected. The value thus obtained may be converted by means of a digital/analog converter 20 into an analog voltage, which is controlled by means of a monitoring member 21 that prevents a given value from being exceeded. If an impermissible condition is established by the monitoring member 21, the latter emits an output signal to an alarm member 22.

It is noted that the band-pass filter in the amplifier 4 used for override of the multiplier 5 by avoiding low frequencies. The pass band of the filter may, for example, be 355–555 kHz.

When samples are taken, very good test results have been obtained with the means described, where it was possible to establish defects in the bearing 2 down to a minimum size of 0.25 μm under a variety of circumstances.

It is noted that the method and means described may be used not only for detecting faults or defects in a bearing, but alternatively, for example, for checking cutting tools for fracture or the like.

The invention is, therefore, not limited to the example described above, which may be varied in different ways within the scope of the invention.

What is claimed is:

1. A method for detecting faults or defects between moving machine parts, wherein mechanical vibrations produced by said faults or defects are converted into an electrical signal from which the conditon of the machine part is obtained, characterized in that for converting the mechanical vibrations into an electrical signal, an acoustic-emission transducer (3) with wide bandwidth is used, a frequency range in the electrical signal being selected by a processing circuit including a multiplier (5) having an oscillator (6) with a frequency of at least 100 kHz connected to the input of the multiplier and having a band-pass filter (4) having a central frequency corresponding to said oscillator frequency, said transducer being connected to the input of said band-pass filter, said multiplier having a low-pass filter (7) connected to the output thereof, where the half wavelengths of said frequency range are smaller than the smallest linear dimension of the cross section of the transducer face which is in contact with the machine part.

2. A method according to claim 1, characterized in that the frequency range is approximately 452–458 kHz.

3. The method of claim 1 wherein said transducer face is round and said dimension is the diameter of said face.

4. A means for detecting faults or defects between moving machine parts such as bearings, comprising a transducer (3) that converts the mechanical vibrations produced by said faults or defects into an electrical signal, and a processing circuit (4–7) that as a function of this signal emits an output signal which indicates the condition of the machine parts, characterized in that the transducer (3) is designed as an acoustic-emission transducer with wide bandwidth and the processing circuit (4–7) selects a frequency range in the transducer signal where the half wavelengths are smaller than the smallest linear dimension of the cross section of the transducer face which is in contact with the machine part, said processing circuit including a multiplier (5) having an oscillator (6) with a frequency of at least 100 kHz connected to the input of the multiplier and having a band-pass filter (4) having a central frequency corresponding to said oscillator frequency, said transducer being connected to the input of said band-pass filter, said multiplier having a low pass filter (7) connected to the output thereof.

5. The means of claim 4, wherein the frequency range is approximately 452–458 kHz.

6. The means of claim 4 wherein said transducer face is round and said dimension is the diameter of said face.

* * * * *